(12) United States Patent
Kunz et al.

(10) Patent No.: US 7,208,301 B2
(45) Date of Patent: Apr. 24, 2007

(54) METHOD FOR PRODUCING 6-0-α-D-GLUCOPYRANOSYL-D-SORBITOL

(75) Inventors: Markwart Kunz, Worms (DE); Mohammad Munir, Kindenheim (DE); Ralf Mattes, Stuttgart (DE); Klaus Dieter Kulbe, Vienna (AT)

(73) Assignee: Südzucker Aktiengesellschaft Mannheim/Ochsenfurt (DE)

( * ) Notice: Subject to any disclaimer, the term of this patent is extended or adjusted under 35 U.S.C. 154(b) by 715 days.

(21) Appl. No.: 10/168,508

(22) PCT Filed: Dec. 27, 2000

(86) PCT No.: PCT/EP00/13283

§ 371 (c)(1),
(2), (4) Date: Feb. 6, 2003

(87) PCT Pub. No.: WO01/48214

PCT Pub. Date: Jul. 5, 2001

(65) Prior Publication Data

US 2004/0209356 A1  Oct. 21, 2004

(30) Foreign Application Priority Data

Dec. 24, 1999  (DE) ............................ 199 63 126

(51) Int. Cl.
 *C12N 9/02* (2006.01)
 *A61K 38/44* (2006.01)
 *C12Q 1/68* (2006.01)

(52) U.S. Cl. .................... 435/189; 424/94.1; 424/94.4; 435/69.1; 435/26; 435/183

(58) Field of Classification Search ..................... None
See application file for complete search history.

(56) References Cited

U.S. PATENT DOCUMENTS

| 5,578,339 | A | * | 11/1996 | Kunz et al. ................. 426/658 |
| 5,747,301 | A | | 5/1998 | Hoshino et al. |
| 5,888,786 | A | | 3/1999 | Niwa et al. |
| 6,127,156 | A | | 10/2000 | Hoshino et al. |

FOREIGN PATENT DOCUMENTS

| DE | 35 02 141 C2- | 8/1991 |
| DE | 690 14 657 T2- | 12/1994 |
| EP | 0 728 840 A2- | 8/1996 |
| EP | 0 897 984 A2- | 2/1999 |
| EP | 0-976 827 | 7/1999 |
| JP | 56029994 | 3/1981 |
| JP | 0056029994 AA- | 3/1981 |
| WO | WO 94/15942- | 7/1994 |
| WO | WO99/20763- | 4/1999 |

OTHER PUBLICATIONS

European Search Report issued Aug. 12, 2005.
Schauder, S., et al., "Polyol Metabolism of Rhodobacter Sphaeroides: Biochemical Characterization of a Short-Chain Sorbitol Dehydrogenase," Society for General Microbiology, Reading, GB, 1995, pp. 1857-1863.
Reuter, R. et al., "Purification and characterization of glucose-6-phosphate dehydrogenase from Pseudomonas W6," Biomedica Miochimica Acta, 1990, 1990, pp. 539-546.
Schneider K-H, et al., "Sorbitol Dehydrogenas from Pseudomonas SP: Purification, Characterization and Application to Quantitative Determination of Sorbitol," Enzyme and Microbial Technology, Stoneham, MA, 1991, pp. 332-337.
Host STN, Datenbank WPIDS AN 1999-608154 (KR 98069057 A).
Meth. Enzymol. 9(1966)170-179.
J. Amer. Chem. Soc. 111(1989) 9275-9276.
Biochemistry 27 (1988) 1622-1628.
Biochem. J. 211 (1983) 81-90.
Chem. Abstr. 115 (199) 44745 (DECHEMA Biotechnol. Conf. (1990), 4, 249-253).
Chem. Abstr. 113 (198) 207154 (DECHEMA Biotechnol. Conf. (1998), 3, 345-349).
Chem. Abstr. 94 (1980) 204476 (Taehan Hwahakhoe Chi 24 (1980) 315-321).
Chem. Abstr. 94 (1980) 79088 (Hanguk Saenghwa Hakhoe Chi 13 (1980) 113-125).
Host STN, Datenbank BIOSIS AN 2000:129479 (Bioscience Biotechnology and Biochemistry 63 (1999) 2137-2143).
Host STN, Datenbank BIOSIS AN 2000: 49098 (Bioscience Bio-Technology and Biochemistry 63 (1999) 1589-1595).
Host STN, Datenbank BIOSIS AN 1997:283999 (Abstracts of The General Meeting of the American Society for Microbiology, 97 (1997), No. 0, pp. 422).
Host STN, Datenbank BIOSIS AN 1991:226372 (Enzyme Microb. Technol. 13 (19991) 332-337).
Host STN, Datenbank BIOSIS AN 1979:193135 (Biotechnol. Bioeng. 20 (1979) 1785-1796).

* cited by examiner

*Primary Examiner*—Michael Pak
(74) *Attorney, Agent, or Firm*—Dickstein, Shapiro, LLP.

(57) ABSTRACT

This invention concerns a method for enzymatic preparation of 6-O-α-D-glucopyranosyl-D-sorbitol (1,6-GPS) from isomaltulose. It is specified that the isomaltulose is put into an aqueous reaction solution containing a unit having sorbitol dehydrogenase (SDH) activity, incubated, and then 1,6-GPS is recovered from the reaction solution.

15 Claims, 2 Drawing Sheets

SEQUENCE LISTING

<160> NUMBER OF SEQ ID NOS: 9

<210> SEQ ID NO 1
<211> LENGTH: 262
<212> TYPE: PRT
<213> ORGANISM: Gluconobacter suboxydans

<400> SEQUENCE: 1

```
Met Ser Lys Lys Phe Asn Gly Lys Val Cys Leu Val Thr Gly Ala Gly
 1               5                  10                  15

Gly Asn Ile Gly Leu Ala Thr Ala Leu Arg Leu Ala Glu Glu Gly Thr
            20                  25                  30

Ala Ile Ala Leu Leu Asp Met Asn Arg Glu Ala Leu Glu Lys Ala Glu
        35                  40                  45

Ala Ser Val Arg Glu Lys Gly Val Glu Ala Arg Ser Tyr Val Cys Asp
    50                  55                  60

Val Thr Ser Glu Glu Ala Val Ile Gly Thr Val Asp Ser Val Val Arg
65                  70                  75                  80

Asp Phe Gly Lys Ile Asp Phe Leu Phe Asn Asn Ala Gly Tyr Gln Gly
                85                  90                  95

Ala Phe Ala Pro Val Gln Asp Tyr Pro Ser Asp Phe Ala Arg Val
            100                 105                 110

Leu Thr Ile Asn Val Thr Gly Ala Phe His Val Leu Lys Ala Val Ser
        115                 120                 125

Arg Gln Met Ile Thr Gln Asn Tyr Gly Arg Ile Val Asn Thr Ala Ser
    130                 135                 140

Met Ala Gly Val Lys Gly Pro Pro Asn Met Ala Ala Tyr Gly Ala Ser
145                 150                 155                 160

Lys Gly Ala Ile Ile Ala Leu Thr Glu Thr Ala Ala Leu Asp Leu Ala
                165                 170                 175

Pro Tyr Asn Ile Arg Val Asn Ala Ile Ser Pro Gly Tyr Met Gly Pro
            180                 185                 190

Gly Phe Met Trp Glu Arg Gln Val Glu Leu Gln Ala Lys Val Gly Ser
        195                 200                 205

Gln Tyr Phe Ser Thr Asp Pro Lys Val Val Ala Gln Gln Met Ile Gly
    210                 215                 220

Ser Val Pro Met Arg Arg Tyr Gly Asp Ile Asn Glu Ile Pro Gly Val
225                 230                 235                 240

Val Ala Phe Leu Leu Gly Asp Asp Ser Ser Phe Met Thr Gly Val Asn
                245                 250                 255

Leu Pro Ile Ala Gly Gly
            260
```

<210> SEQ ID NO 2
<211> LENGTH: 789
<212> TYPE: DNA
<213> ORGANISM: Gluconobacter suboxydans

```
<400> SEQUENCE: 2
atgtcgaaga agtttaacgg taaagtctgt ctggtcaccg gcgcgggtgg caatattggt    60
cttgcgaccg ccctccgtct ggcagaagag ggcacggcca tcgcccttct ggacatgaac   120
cgcgaggcgc tggaaaaggc ggaagcctcc gtccgtgaaa agggcgtcga agcccgctcc   180
tatgtctgtg acgtcacgtc cgaagaggcc gtgatcggga cggtggatag cgtggtccgg   240
gacttcggga agatcgactt cctgttcaac aatgccggct atcagggcgc cttcgccccc   300
gtgcaggact acccgtccga cgatttcgcg cgcgtgctga cgatcaacgt caccggtgcc   360
ttccacgtcc tcaaagccgt ttcgcgccag atgatcacgc agaactacgg cgcatcgtc    420
aacaccgcca gcatggccgg tgtgaaggga ccgccaaaca tggccgccta tggtgcgtcc   480
aagggcgcca tcatcgccct gaccgaaacg gccgcgcttg accttgcccc ctacaacatc   540
cgtgtgaacg ccatcagccc cggttacatg gggcccggtt tcatgtggga cgtcaggtc    600
gagcttcagg ccaaggtcgg aagccagtat ttctccaccg atcccaaggt cgtggcccag   660
cagatgatcg gcagcgttcc gatgcgccgc tatggcgaca tcaacgagat cccgggcgta   720
gtagcgttcc tgctggggga tgattccagc ttcatgacgg gggtgaacct gccgattgct   780
ggcggttga                                                           789

<210> SEQ ID NO 3
<211> LENGTH: 29
<212> TYPE: PRT
<213> ORGANISM: Gluconobacter suboxydans

<400> SEQUENCE: 3

Lys Lys Phe Asn Gly Lys Val Cys Leu Val Thr Gly Ala Gly Asn
  1               5                  10                  15
Ile Gly Leu Ala Thr Ala Leu Arg Leu Ala Glu Glu Gly
             20                  25

<210> SEQ ID NO 4
<211> LENGTH: 14
<212> TYPE: PRT
<213> ORGANISM: Gluconobacter suboxydans

<400> SEQUENCE: 4

Val Leu Thr Ile Asn Val Thr Gly Ala Phe His Val Leu Lys
  1               5                  10

<210> SEQ ID NO 5
<211> LENGTH: 12
<212> TYPE: PRT
<213> ORGANISM: Gluconobacter suboxydans

<400> SEQUENCE: 5

Gly Pro Pro Asn Met Ala Ala Tyr Gly Ala Ser Lys
  1               5                  10

<210> SEQ ID NO 6
<211> LENGTH: 13
<212> TYPE: PRT
<213> ORGANISM: Gluconobacter suboxydans

<400> SEQUENCE: 6

Val Val Ala Gln Gln Met Ile Gly Ser Val Pro Met Arg
  1               5                  10

<210> SEQ ID NO 7
```

-continued

```
<211> LENGTH: 17
<212> TYPE: PRT
<213> ORGANISM: Gluconobacter suboxydans

<400> SEQUENCE: 7

Val Asn Ala Ile Ser Pro Gly Tyr Met Gly Pro Gly Phe Met Ser Glu
 1               5                  10                  15

Arg

<210> SEQ ID NO 8
<211> LENGTH: 11
<212> TYPE: PRT
<213> ORGANISM: Gluconobacter suboxydans

<400> SEQUENCE: 8

Val Gly Ser Gln Tyr Phe Ser Thr Asp Pro Lys
 1               5                  10

<210> SEQ ID NO 9
<211> LENGTH: 21
<212> TYPE: PRT
<213> ORGANISM: Gluconobacter suboxydans

<400> SEQUENCE: 9

Ser Tyr Val Cys Asp Val Thr Ser Glu Glu Ala Val Ile Gly Thr Val
 1               5                  10                  15

Asp Ser Val Val Arg
                20
```

METHOD FOR PRODUCING 6-0-α-D-GLUCOPYRANOSYL-D-SORBITOL

This concerns a method for enzymatic preparation of 6-0-α-D-glucopyranosyl-D-sorbitol (1,6-GPS) from isomaltulose or sucrose and means for conducting this method.

BACKGROUND

There are known methods for producing 1,6-GPS from sucrose that include enzymatic conversion of sucrose to isomaltulose followed by chemical hydrogenation of the resulting isomaltulose to the two stereoisomers 1,6-GPS and 1-0-α-D-glucopyranosyl-D-mannitol (1,1-GPM).

A sucrose isomerase that catalyzes the conversion of sucrose to isomaltulose is known from DE 44 14 185 C1.

Schiweck (alimenta 19 (1980), 5–16) discloses the enzymatic conversion of sucrose to isomaltulose and subsequent hydrogenation to the isomaltulose on Raney nickel catalyst to Palatinit® (also called isomalt), a nearly equimolar mixture of 1,6-GPS and 1,1-GPM. The publication describes the preparation of isomaltulose by transglucosidation of sucrose by *Protaminobacter rubrum*. In addition, how the isomaltulose produced by microorganisms is converted in the presence of Raney nickel catalysts to 1,6-GPS and 1,1-GPM by hydrogenation and can then be enriched by evaporation and cooling crystallizations is disclosed.

DE 197 01 439 A1 discloses a method for hydrogenation of isomaltulose by means of a carrier-bound nickel substrate, with mixtures of 1,6-GPS and 1,1-GPM being obtained.

DE 197 05 664 A1 describes a method for producing 1,6-GPS and 1,1-GPM enriched mixtures. This publication discloses a method in which 1,6-GPS and/or 1,1-GPM enriched mixtures are obtained from hydrogenated isomaltulose or from mixtures that contain hydrogenated isomaltulose. It is possible by means of this method to produce 1,6-GPS in pure form, by concentrating and cold-crystallizing 1,6-GPS-rich mother solution under certain conditions.

DE 195 23 008 A1 discloses a method for producing 1,1-GPM and 1,6-GPS. The document describes how various catalysts are used at pressures under 50 atmospheres so that mixtures of 1,6-GPS and 1,1-GPM are obtained by hydrogenation of isomaltulose. The disclosed catalyst on which the isomaltulose is converted contains ruthenium, nickel and their mixtures.

Methods for obtaining sugar alcohol mixtures containing 1,1-GPM and 1,6-GPS by enzymatic rearrangement of sucrose to isomaltulose and trehalulose and subsequent hydrogenation to 1,1-GPM, 1,6-GPS and 1-0-α-D-glucopyranosyl-D-sorbitol (1,1-GPS) follow from EP 0 625 578 B1.

The methods according to the prior art are seen as disadvantageous above all for two reasons. First, with the current methods one can only obtain mixtures of 1,6-GPS and 1,1-GPM, from which the substance of interest (1,6-GPS or 1,1-GPM) then has to be isolated by costly chemical and physical separation methods. Second, it is not possible to conduct the overall process of converting sucrose to the desired end products in a single process step. Thus in the prior art quite complicated process sequences are necessary for the production of 1,6-GPS from sucrose, employing various physical, chemical and biological process steps in different reactors. Catalysts, special hydrogenation reactors and technical hydrogen are necessary according to the current state of the art for the hydrogenation of isomaltulose. An important disadvantage of the known hydrogenation of isomaltulose to 1,6-GPS and 1,1-GPM thus lies in the required industrial expenditure. Frequently, pressures of roughly 50 to over 100 atmospheres are necessary for the hydrogenation, which necessitates a specific equipment design. Since the resulting products are used as a rule in the food industry, the process operations additionally have to be chosen so that no toxic materials, for example the catalysts, get into the end products of the hydrogenation reaction. The product that is formed is a mixture of the important components 1,6-GPS and 1,1-GPM, from which the substance of interest in each case has to be separated by chemical and chemical-physical purification methods. To obtain chemically pure 1,6-GPS or 1,1-GPM, costly enrichment and isolation procedures are thus necessary after the chemical hydrogenation. The yield of these process steps is frequently unsatisfactory.

The industrial problem underlying this invention thus consists of making available a process and a means for conducting it that enable a simple, cheap and selective preparation of 1,6-GPS from isomaltulose.

SUMMARY

This invention solves this industrial problem by making available a method for enzymatic preparation of 1,6-GPS from isomaltulose, where the isomaltulose is put into an aqueous reaction solution containing a unit having sorbitol dehydrogenase (SDH) activity and incubated and 1,6-GPS is recovered from the reaction solution. The invention thus enables isomaltulose to be hydrogenated biochemically or enzymatically to 1,6-GPS by means of a unit having SDH activity. The unit having SDH activity that is used in accordance with the invention reduces isomaltulose specifically to 1,6-GPS. The unit having SDH activity is characterized by the fact that it is capable of converting isomaltulose or mixtures containing isomaltulose enzymatically to 1,6-GPS or mixtures containing 1,6-GPS. The advantage of the enzymatic conversion of isomaltulose to 1,6-GPS, besides the simplified procedure that is thus enabled, lies in the high reaction and substrate specificity and stereospecificity, in the uniformity of the reaction product, in the savings of energy of raw materials and in its environmental compatibility.

The invention thus concerns the surprising teaching that means of a specific enzymatic process 1,6-GPS can be produced in an entirely targeted fashion from isomaltulose. In accordance with the invention the educt isomaltulose is put into an aqueous reaction solution that contains a unit having sorbitol dehydrogenase (SDH) activity and incubated until 1,6-GPS is formed and can be recovered from the reaction solution by means of traditional methods, for example crystallization.

In connection with this invention an aqueous reaction solution is understood to mean unbuffered water or water buffered with traditional buffer systems, in which in each case according to the starting conditions and target conditions additives like stabilizers, indicator systems, reduction equivalents, regeneration agents, nutrient components, solids, sugars, sugar alcohols, etc., are contained.

DETAILED DESCRIPTION OF THE INVENTION

In a preferred embodiment of the invention the unit having SDH activity is the enzyme SDH. For the enzymatic conversion of isomaltulose to 1,6-GPS in accordance with the invention it is possible to introduce the unit having SDH activity, thus the enzyme SDH, into the reaction solution in purified, enriched and/or isolated form, where the enzyme can, for example, be of natural origin. Of course, the SDH used in accordance with the invention can also be a recombinantally produced SDH in accordance with the invention from an organism modified by genetic engineering. It is advantageous to use isolated SDH when tests of the kinetics of the conversion of isomaltulose to 1,6-GPS for purposes of optimizing this reaction are to take place. In particular, all matters having to do with the chemical equilibrium of the conversion of isomaltulose to 1,6-GPS require operation with isolated enzymes, since otherwise the stoichiometry, dissociation constants, matters of inhibition or activation of the enzyme, problems of cooperativity, initial rate, conformation, ligands and all other problems of enzyme kinetics and the binding data of interest cannot be analyzed with sufficient precision. Especially in order to affect the reaction in a targeted way, it is advantageous that the unit having SDH activity be in isolated form, since otherwise one cannot preclude that because of interactions with other components of the reaction solution, the results of modifications of pH, ion concentration and temperature will not be reproducible, since purified, partially purified and cell-bound enzymes show diverging values in analysis.

The invention accordingly also concerns a method for partial or complete isolation of an SDH from microorganisms, especially for microorganisms of the genus *Gluconobacter*, especially the species *Gluconobacter suboxidans*, where in a first step the microorganisms are digested by conventional methods and homogenized to a raw extract, in a second step a separation of the raw extract takes place by means of anion exchange chromatography, in a third step filtration and in a fourth step a dye affinity chromatography takes place. Preferably, it is provided in accordance with the invention that partially purified enzyme obtained after the dye affinity chromatography is purified until homogeneous by means of chromate focusing or in another preferred embodiment by means of another dye affinity chromatography followed by affinity elution with at least one reduction equivalent.

In a particularly preferred embodiment of this invention the invention concerns a method for isolating SDH from a microorganism, where the microorganism is digested in a first step and homogenized to a raw extract, in a second step the resulting raw extract is subjected to anion exchange chromatography, in a third process step it is subjected to a first dye ligand affinity chromatography and in a fourth process step it is subjected to a second dye ligand chromatography. In an especially preferred embodiment the invention concerns a method of a said kind, where an ultrafiltration is carried out after the first and before the second dye ligand affinity chromatography. In an especially preferred embodiment an affinity elution of the pure SDH is carried out at the end of the method given above, thus after the second dye ligand affinity chromatography, using one reduction equivalent, in particular NADH, for this.

In another preferred embodiment the unit having SDH activity is an SDH-containing dead or living microorganism or a homogenate thereof. The reaction specified preferably in accordance with the invention with dead, especially preferably dried, microorganisms takes place in a preferred embodiment of this invention after rehydration of these microorganisms in the presence of an SDH enzyme solution by standard methods, for example while adding tannin and/or glutaraldehyde, and is advantageous since the soluble enzyme rearranges the microorganism under solid conditions in a high concentration. Of course, the rehydration can also be carried out with water or a special rehydration can be omitted entirely, so that the dead organisms are introduced directly into the aqueous reaction solution. The conversion of isomaltulose with vital microorganisms that is also specified in accordance with the invention has, among other things, the advantage that it can occur at relatively low cost.

Bioreactors in which microorganisms are used are as a rule generally usable and, compared to the chemical catalytic conversions of isomaltulose to 1,6-GPS, have lower energy and maintenance costs. Of course, the reaction conditions (pH value, ion concentration, oxygen/carbon dioxide demand, trace elements, temperatures and the like) have to be chosen so that the microorganisms are capable of optimum conversion of isomaltulose to 1,6-GPS. Under these process conditions the SDH in a natural microenvironment, thus within the cell, can have higher stability and efficacy than the isolated enzyme. In addition, under suitable conditions cell propagation and thus an increase of the SDH concentration can be possible. Compared to the prior art, according to which one must operate with costly catalyst and technical hydrogen, the enzymatic conversion by means of microorganisms thus means an important advantage, which concerns reliability, automation and simplicity as well as quality and yield of the end product of the method.

In accordance with the invention it is intended in a preferred embodiment of the invention to separate certain cell compartments or parts thereof from each other or to combine them. Carbohydrate structures, lipids or proteins and/or peptides as well as nucleic acids that are capable of having a positive or negative effect on the unit or enzyme having SDH activity can thus be combined or separated. In order to get around this influence or to use it in a targeted way raw extracts are made from the microorganisms. This can take place by means of sonication, pressing, homogenization, mixing with glass beads, through detergents, the effects of electrical fields, by mechanical processing in liquid nitrogen or by enzymatic digestion of the cell membrane and wall. In another step the resulting extract can in a preferred embodiment be centrifuged in order to carry out the conversion in accordance with the invention with the supernatant or the sediment. The preparation of the raw extract additionally has the advantage that the ratio of nucleic acids to enzyme can be determined by simply measuring the extinction. Under certain process conditions it can be specifically necessary to separate the nucleic acids, since these complexes can accompany the unit having SDH activity and thus reduce the efficiency of the conversion of isomaltulose to 1,6-GPS. The preparation of a raw extract in the sense of this invention also includes all of the measures that stabilize the raw extract or optimize its catalytic action. This can include the addition of protamine sulfate, manganese chloride and lysozym as well as modification of the ion strength and all measures that serve to modify the protease activity of the raw extract in accordance with the invention so that the unit having SDH activity is stabilized and optimized in its effect.

In another preferred embodiment the microorganism containing SDH or the organism from which the completely or partially purified SDH derives is an organism of the genus *Gluconobacter*, especially *Gluconobacter suboxidans*, especially preferably *Gluconobacter suboxidans* DSM 2003. A very good yield of 1,6-GPS can be achieved especially in the combination preferably called for in accordance with the invention with the coenzyme regeneration system SDH/FDH (formate dehydrogenase). However, the enzymatic conversion by microorganisms is in no way restricted to these two strains. All organisms, especially microorganisms that are capable of converting isomaltulose to 1,6-GPS in one or more steps, can be used in accordance with the invention, for example fungi, yeasts, cell cultures, etc. One can count among these mutants derivatives of the said organisms that have been modified by genetic engineering or otherwise prepared or isolated, for example organisms that have SDH activity because of the insertion of an SDH-coding nucleotide sequence. Organisms that also have a sucrose mutase activity are preferred, so that sucrose can be enzymatically converted to 1,6-GPS by means of a single type of organism.

In another preferred embodiment the units having SDH activity in accordance with the invention, especially microorganisms, raw extracts, parts thereof and/or the enriched or isolated enzymes are immobilized. Through immobilization enzymes, cell organelles and cells are put into an insoluble and reaction space-limited state. In accordance with the invention the unit having SDH activity is immobilized under conditions under which it has SDH enzyme activities that are as high as possible. The inclusion of vital cells in polymers is also intended in accordance with the invention. The immobilization can take place by (i) binding and also by (ii) inclusion. In a binding immobilization of the unit having SDH activity carrier compounds (ionic or covalent) and cross-linkings (liking with each other with other polymers) are present. In an inclusion immobilization of the unit having SDH activity inclusion into gel structures (beads, fibers and the like) and in membranes (microcapsules and membrane reactors) is intended. Immobilization is accordingly understood to mean all methods that serve to limit the mobility and solubility of the units having SDH activity by biological, chemical or physical means. This can take place in particular by adsorption on inert or electrically charged, inorganic or organic carrier materials, where the inorganic materials are, for example, porous glasses, silica gel, aluminum oxide and hydroxyapatite or metal oxides; the natural polymers can be, for example, cellulose, starch, dextran or agarose and the synthetic polymers can be polyacrylamide, polyvinyl alcohol, nylon or others. It is also intended in accordance with the invention to include the unit having SDH activity into a three-dimensional network; in one embodiment of the invention this can be gelatin or agar. In addition, it can be intended to carry out the immobilization by means of cross-liking with bifunctional agents like glutaric dialdehyde or benzidine. A microencapsulation of the unit having SDH activity that leads to restriction of the reaction space by means of artificial or biological membranes is also possible. The invention also encompasses an immobilization without a carrier by flocculation and "cross-linking" as well as coimmobilization of living and/or dead cells with free or immobilized enzymes. Also, an increase of molecular weight, for example by binding to dextran, serves for immobilization in the sense of the invention. The immobilized enzyme can be an enzyme, which is bonded to compartments of a microorganism or to a complete vital or dried microorganism, but in the sense of the invention immobilized can also mean that the enzyme is bonded to a carrier by itself or that the enzyme is bonded to a carrier in combination with compartments of the organism. It is important that the charged matrix can come into contact with the isomaltulose so that the desired enzymatic reaction to 1,6-GPS takes place. However, of course, the invention also concerns the use of the said unit having SDH activity in free, i.e., not immobilized, form.

In another preferred embodiment the enzymatic conversion in accordance with the invention is carried out with or without pH regulation. In particular, since reduction equivalents in the form of hydrogen transfer agents are used in a particularly preferred embodiment, the choice of the pH value affects the equilibrium of the chemical reaction as well as the overall yield of 1,6-GPS. Accordingly, the enzymatic conversion of isomaltulose to 1,6-GPS can be divided into the reactions in which there is no regulation of the pH value and those in which the pH value is regulated. The regulation of the pH value can take place by the addition or feed of substances that are capable of raising, lowering or stabilizing the pH value. In accordance with the invention acids or bases according to the Lowry-Bronsted or Lewis-Pearson definition can be used, whereby protons, hydronium ions, hydroxide ions or free electron pairs can be released or made available, or absorbed. For example, the aqueous reaction solution can be injected with $CO_2$, which, like the feed of an acid, is a measure for regulating the pH value. One can advantageously strive to set the pH value in a range that is seen as optimum for the activity of the enzyme. This optimum pH can be reached through various buffers or through the addition of pH-lowering or pH-raising substances. However, all-in-all regulation of the pH is not in any way limited to chemical methods such as complexing operations, titrations or the like. Any intervention into the system that leads to the pH value being regulated or stabilized in any way can be considered as carrying out a pH regulation in the sense of the invention. In an advantageous embodiment of the invention the pH value of the aqueous solution is about 6.0 to 8.0, preferably 7.0.

In a preferred embodiment of the invention reduction equivalents are also added to the aqueous reaction solution in addition to the unit having SDH activity, especially when purified and isolated SDH is used. Reduction equivalents in the sense of this invention are hydrogen carriers or electron carriers that can be in the form of coenzymes or prosthetic groups. Such reduction equivalents can be, for example, $NAD^+/NADH$, $NADP^+/NADPH$, $FMN/FMNH_2$ or $FAD/FADH_2$. Coenzymes and prosthetic groups of oxidoreduction reactions serve as hydrogen and/or electron carriers that are disassociatable and/or firmly bonded to proteins. However, other coenzyme/prosthetic groups that are capable of carrying hydrogen atoms or electrons can also serve as reduction equivalents. Preferred in accordance with the invention are in particular cyclic tetrapyrroles, glutathione, lipoic acid, quinones, iron-sulfur proteins, flavoproteins, flavin nucleotides and all others that can carry protons, atoms and/or electrons for functional groups during the enzymatic catalysis.

Living cells having SDH activity are preferably used for enzymatic production of 1,6-GPS, so that the addition of reduction equivalents becomes unnecessary.

In another especially preferred embodiment the enzymatic conversion of isomaltulose to 1,6-GPS takes place in the presence of regeneration agents like formate dehydrogenase (FDH) and/or formate, especially when purified and isolated SDH is used. Through the addition of SDH and FDH to the aqueous reaction solution a chemical reaction is possible during which formate is continuously converted to $CO_2$ and isomaltulose to 1,6-GPS. The conversion of the formate to $CO_2$ takes place via the FDH. The hydrogen atoms absorbed in this oxidation by a reduction agent that is optionally present in the reaction solution, for example NAD$^+$, are used in the parallel reduction of isomaltulose to 1,6-GPS. Of course, completely other dehydrogenases or enzymes with other substrate specificities can also be possibilities as coenzyme of the regeneration system, thus as regeneration agents. For example, other carboxylic acids or their salts can be used as regeneration agents. It is important that the added substances, especially FDH/formate, are capable of reacting with hydrogen carriers, coenzymes or prosthetic groups so that electrons and/or hydrogen atoms are transferred so that continuous formation of 1,6-GPS is possible. If living cells are used as the unit having SDH activity, the addition of regeneration agents and reduction equivalents can be omitted.

In another especially preferred embodiment the conversion of isomaltulose to 1,6-GPS takes place within the scope of a continuous process. The continuous process of the invention can be carried out in a flow-through reactor in which microbial growth and thus production formation, the synthesis of 1,6-GPS, takes place. In this way very large amounts of 1,6-GPS can be produced. Through the use of the continuous process the purification and preparation cycles can be freely chosen and are not specified by the parameters of specific fermenters or specific physiological properties of the microorganisms, since in continuous systems the environment surrounding the microorganisms is not altered by the consumed substances and resulting products, since the products are continuously withdrawn and the substrates are continuously supplied. In addition, the bioreactors or plants in a continuous process are designed to be much smaller and cheaper. A continuous process is also understood in the sense of the invention to include all supplemental measures that serve to prevent the danger of infection with other organisms which can rapidly spread in the system through substrate locking. This can include sterile as well as nonsterile conditions. This invention also concerns process steps and means that serve to create continuous fermentation through extreme conditions so that they are stable with regard to possible infections because of the selected extreme conditions (for example buffering at very low pH value or the feed of antibiotics). Here it is possible in accordance with the invention to use deviations or modifications of the said units having SDH activity that are matched to these infection-hostile conditions, for example antibiotic resistant microorganisms. Under a continuous process in the sense of this invention, however, one can also understand any system of growing cells and catalyzing enzymes to which a nutrient solution is in turn supplied and from which on the other hand a culture solution including the enzymatically produced 1,6-GPS is withdrawn; these can be both homogeneous as well as inhomogeneous systems.

Of course, the invention concerns semi-continuous or batchwise processes.

In another preferred embodiment the isomaltulose, which is the starting material for the reaction of conversion to 1,6-GPS is produced by enzymatic conversion of sucrose. The isomaltulose used in the method in accordance with the invention can be produced from sucrose by enzymatic conversion (transglucosidation) by means of purified or enriched enzymes, raw extracts or microorganisms that have sucrose mutase activity. In connection with this invention sucrose mutase is thus understood to mean an enzyme that is capable of isomerization of sucrose to isomaltulose and is also known as sucrose isomerase.

Examples of cells that contain nucleotide sequences coding for a protein with sucrose mutase activity are in particular microorganisms of the genera *Protaminobacter,* *Erwinia, Serratia, Leuconostoc, Pseudomonas, Agrobacterium, Klebsiella* and *Enterobacter*. Specific examples of such microorganisms are *Protaminobacter rubrum* (CBS 547,77), *Erwinia rhapontici* (NCPPB 1578), *Serratia plymuthica* (ATCC 15928), *Serratia marcescens* (NCIB 8285), *Leuconostoc mesenteroides* NRRL B-521f (ATCC 10830a), *Pseudomonas mesoacidophila* Mx-45 (FERM 11808, or FERM BP 3619), *Agrobacterium radiobacter* MX-232 (FERM 12397, or FERM BP 3620), *Klebsiella* subspecies and *Enterobacter* species.

Specific examples of proteins with sucrose mutase activity and nucleic acids coding for it from *P. rubrum, E. Rhapontici, Enterobacter* spec. SZ62 and *P. mesoacidophila* are described in PCT/EP 95/00165.

The said cells or proteins or nucleotide sequences from these cells can be used together with a unit of this invention having SDH activity to produce 1,6-GPS from sucrose, for example, by inserting an expressing SDH coding nucleotide sequences into the said cells under control of regulator units.

In a particularly preferred embodiment the enzymatic conversion of sucrose to isomaltulose is carried out by means of, preferably, immobilized *P. rubrum* cells (*Protaminobacter rubrum*) or digested cell material or raw extract *P. rubrum*, or by means of partially or completely purified sucrose mutase (also sucrose isomerase). This reaction preferably takes place together in a reaction solution with the SDH-dependent conversion of isomaltulose to 1,6-GPS.

The enzymatic rearrangement of sucrose to isomaltulose is described, for example, in DE 195 23 560 A1 or DE 44 14 185 C1, which are incorporated completely into the disclosure content of this application with regard to the microorganisms, DNA sequences, enzymes and methods for producing isomaltulose from sucrose by enzymatic conversion that are disclosed there.

The immobilization of cells that have sucrose mutase, for example *P. rubrum* from cell digests thereof or from the isolated enzyme (sucrose mutase) serves to restrict the mobility and solubility of the biocatalysts that are used in a biological, chemical and/or physical way. Immobilization in the sense of the invention can take place by various methods, for example binding of the biocatalysts to each other or to carriers, by fixation in the network of a polymer matrix or by surrounding with artificial or natural membranes, which of course includes the use of inverse micelles. By immobilizing the cells, the cell digests or/and the sucrose mutase the resulting biocatalysts are not only reusable, they can above all easily be separated after or during the process in order to replace them optionally by other catalysts that catalyze other reactions such as the conversion of isomaltulose to 1,6-GPS. An important advantage is that cells or enzymes can be used in much higher local concentrations and above all in continuous flow-through systems. The immobilization here can take place on ceramic carriers, polymers, various gels and gelatins, by inclusion in polyarylamide or other methods.

In another preferred embodiment the conversion of sucrose to isomaltulose and of isomaltulose to 1,6-GPS takes place in a single process step, i.e., the two enzymatic conversion reactions progress simultaneously or slightly time-shifted in one and the same aqueous reaction solution. The conversion of sucrose to 1,6-GPS can therefore take place in one process step, since the two individual reactions can progress enzymatically under the same or similar process conditions.

In another preferred embodiment the conversion of sucrose to 1,6-GPS takes place in a single bioreactor (a so-called "one-pot reaction").

These embodiments of the invention consist of direct enzymatic production of 1,6-GPS from sucrose, where the said nonimmobilized and immobilized cells, raw extracts and/or enzymes, which thus have SDH and sucrose mutase activities, can be used both for the conversion of sucrose to isomaltulose and for the conversion of isomaltulose to 1,6-GPS.

In accordance with the invention the conversion is also possible in a batch and/or fed batch fermentation (a discontinuous fermentation), where the nutrient medium is inoculated at a specific time point and the fermentation is ended after consumption of the limiting substrate, which can be, for example, sucrose, other substrates or enzymes/coenzymes, or at another appropriate point in time. However, the reaction conditions can also be chosen so that the limiting effect of a substrate is largely excluded. Batch reactions can be carried out in a so-called closed system. These systems are also to be interpreted as closed systems in accordance with the invention when oxygen, air or another gas or gas mixture is continuously supplied to the closed liquid phase. In a batch process the environment of the cells continuously changes, since there can be a decrease of the amount of substrate and, among other things, an increase of the amount of 1,6-GPS and, under certain circumstances even an increase of the cell concentration. The said "one-pot process" can also be carried out as a continuous enzymatic catalysis in the sense of the invention while maintaining a flow equilibrium—with continuous removal of 1,6-GPS.

In another preferred embodiment the temperature of the aqueous reaction solution is 20° C. to 40° C., especially 25° C., in the enzymatic conversion. At temperatures of 25° C. the purified SDH has stability of about a week. Thus, temperatures in this range are well-suited for conducting long-term enzyme-catalyzed processes.

In another preferred embodiment the invention concerns a method for producing 1,6-GPS from sucrose, where the sucrose is first enzymatically converted to isomaltulose and then the isomaltulose is enzymatically converted to 1,6-GPS. This overall operation can progress continuously, semi-continuously or not continuously, in one or more process steps and in one or more bioreactors.

The invention also concerns a nucleic acid molecule in coding an enzyme with the activity of a sorbitol dehydrogenase (SDH) selected from the group consisting of a) nucleic acid molecules that encode a protein that has the amino acid sequence given under SEQ ID No. 1 or a complimentary strand thereof;

b) nucleic acid molecules that include the nucleotide sequence represented under SEQ ID No. 2 or a complimentary strand thereof;

c) nucleic acid molecules that hybridize with a nucleic acid molecule given under (a) or (b);

d) nucleic acid molecules whose nucleotide sequence deviates from the sequence of the nucleic acid molecules given under (b) or (c) because of degeneration of the genetic code.

In connection with this invention an enzyme with sorbitol dehydrogenase activity is understood to mean a protein or peptide that is capable of catalyzing the conversion of isomaltulose to 1,6-GPS. The isomaltulose to be converted can derive from the enzymatic conversion of sucrose.

The nucleic acid molecules in accordance with the invention can be isolated from natural sources, preferably from *Gluconobacter* spec., or can be synthesized by known methods. It is possible by means of current molecular biological techniques to insert various mutations into the nucleic acid molecules in accordance with the invention, which results in the synthesis of enzymes with possibly altered biological properties, which are likewise encompassed by the invention. Mutations in the sense of the invention also concern all deletion mutations that lead to truncated enzymes. Through other molecular mechanisms like insertions, duplications, transpositions, gene fusion, nucleotide exchange and also through gene transfer between different microorganism strains and other mechanisms there can occur, for example, modifications of the enzyme activity and/or the regulation of the enzyme. In this way mutant enzymes, for example, can be produced that have an altered $K_m$ value, $K_i$ value, or $K_a$ value and/or are no longer subject or are subject in modified form, to the regulation mechanisms normally present in the cells. Moreover, in accordance with the invention mutant enzymes can be produced that have altered stability, substrate specificity, product specificity or an altered effect or pattern or a modified activity, temperature, pH value and/or concentration profile. In addition, the teaching in accordance with the invention concerns enzymes that have an altered active enzyme concentration, a modified structure of subunits, pre- and posttranslational modifications, for example signal and/or transport peptides and/or other functional groups.

The invention also concerns nucleic acid molecules that hybridize with the said nucleic acid molecules in accordance with the invention. Within the scope of the invention hybridization means a hybridization under conventional hybridization conventions, as described in Sambrook et al. (Molecular Cloning. A laboratory manual, Cold Spring Harbor Laboratory Press, $2^{nd}$ ed., 1989), preferably under stringent conditions. In accordance with the invention one speaks of a hybridization when after washing for 1 h with 1×SSC and 0.1% SDS at 55° C., preferably at 62° C. and especially preferably at 68° C., in particular for 1 h in 0.2×SSC and 0.1% SDS at 55° C., preferably at 62° C. and especially preferably at 68° C., a positive hybridization signal is still observed.

A nucleotide sequence hybridizing under such wash conditions with one of the nucleotide sequences given in the sequence protocol is a nucleotide sequence in accordance with the invention.

The identification and isolation of such nucleic acid molecules can take place with the use of the nucleic acid molecules in accordance with the invention or parts of these molecules or the complimentary strand. Nucleic acid molecules that have exactly or essentially the nucleotide sequence represented in SEQ ID No. 2 or parts of this sequence, for example, can be used as hybridization probes. The fragments used as hybridization probes can also be synthetic fragments, which are prepared by means of conventional synthesis techniques and whose sequence essentially corresponds with that of a nucleic acid molecule in accordance with the invention. The molecules hybridizing with the nucleic molecules in accordance with the invention also comprise fragments, derivatives and allelic variants of the nucleic acid molecules described above that encode an enzyme in accordance with the invention. "Fragments" are understood to mean parts of the nucleic acid molecules that are long enough to code for the described enzyme. The term "derivative" in connection with this invention means that the sequences of this molecule differ from the sequences of the nucleic acid molecule described above at one or more positions, but have a high degree of homology to these sequences. Homology here means sequence identity of at least 40%, especially an identity of at least 60%, preferably over 80% and especially preferably over 90%, 95%, 97% or 99% at the nucleic acid level. Here the enzymes encoded by these nucleic acid sequences have a sequence identity to the amino acid sequence given in SEQ ID No. 1 of at least 80%, preferably 85% and especially preferably over 90%, 95%, 97%, and 99% at the amino acid level. Deviations to the nucleic acid molecules described above can result, for example, through deletion, substitution, insertion or recombination. These can be both naturally occurring variants, for example, sequences from other organisms, or mutations, where these mutations can arise naturally or can have been inserted by targeted mutagenesis (UV or x-ray radiation, chemical agents, etc.). In addition, the variations can be synthetically produced sequences. The allelic variants can be both naturally occurring variants as well as synthetically prepared variants or variants produced by recombinant DNA techniques. The enzymes encoded by the different variants of the nucleic acids in accordance with the invention have certain common characteristics like enzyme activity, active enzyme concentration, subunits, posttranslational modifications, functional groups, molecular weight, immunological reactivity, conformation and/or physical properties like the flow behavior in gel electrophoresis, chromatic behavior, sedimentation coefficients, solubility, spectroscopic properties, stability, pH optimum, isoelectric pH value, temperature optimum and/or others.

The nucleic acid molecules in accordance with the invention can be both DNA and RNA molecules. DNA molecules in accordance with the invention are, for example, genomic DNA or cDNA molecules.

The invention further concerns vectors that contain nucleic acids in accordance with the invention. Preferably these are plasmids, cosmids, viruses, bacteriophages, shuttle vectors and other vectors that are common in genetic engineering. The vectors in accordance with the invention can have still other functional units that bring about or contribute to stabilization and/or replication of the vector in a host organism.

Vectors with which the nucleic acid molecule in accordance with the invention is operatively bound to at least one regulatory element that ensures transcription and synthesis of translatable nucleic acid molecules in procaryotic and/or eucaryotic cells are contained in accordance with the invention in a particular embodiment. Such regulatory elements can be promotors, enhancers, operators and/or transcription termination signals. Of course, the vectors can also contain elements necessary for their stability and/or replication as well as antibiotic resistant genes, thus selection markers.

The invention also concerns the said vectors, where these vectors contain, besides the nucleic acid sequence that encodes an SDH and that is under the control of at least one regulatory element, a nucleic acid sequence that encodes sucrose mutase and that is likewise under the control of at least one regulatory element. Such a vector thus has the genetic information for the two enzymes that are necessary for enzymatic conversion of sucrose to 1,6-GPS via isomaltulose. Such vectors make it possible to utilize the metabolic apparatus of a single host organism in a particularly simple way in order to convert sucrose enzymatically to 1,6-GPS in a single process step.

The invention also concerns host cells that contain one of the nucleic acid molecules in accordance with the invention or one of the vectors in accordance with the invention or are transformed with them and preferably are capable of expressing SDH and optionally the sucrose mutase as well as especially preferably producing 1,6-GPS from isomaltulose or sucrose. In addition, the invention concerns all host cells that derive from a host cell transformed with the nucleic acid molecules in accordance with the invention or the vectors in accordance with the invention. The invention thus concerns host cells that contain the nucleic acid molecules or vectors in accordance with the invention, where a host cell is understood to mean an organism that is capable of absorbing recombinant nucleic acid molecules in vitro and optionally synthesizing the enzymes encoded by the nucleic acid molecules in accordance with the invention. Preferably, they are procaryotic or eucaryotic cells. Above all, the invention concerns microorganisms that contain the vectors, derivatives or parts of vectors in accordance with the invention that enable these vectors, derivatives or parts of vectors to synthesize enzymes for the preparation of 1,6-GPS from isomaltulose or from sucrose. The host cells in accordance with the invention can also be characterized by the fact that the nucleic acid molecule introduced in accordance with the invention is either heterologous in reference to the transformed cell, i.e., does not naturally occur in this cell, or is localized at a different site or a different copy number in the genome than the corresponding naturally occurring sequence.

In one embodiment of the invention this cell is a procaryotic, preferably a gram negative procaryotic cell, especially preferably an enterobacterium cell. On the one hand a cell that does not contain inherent SDH and/or sucrose mutase gene, for example *E. coli*, can be used, but on the other hand it is also possible to use cells that already contain one or two such genes in their chromosome. Preferred examples of suitable procaryotic cells are *E. coli, Protaminobacter rubrum, Erwinia rhapontici, Enterobacter* spec., or *Pseudomonas mesoacidophila* cells. Transformation of procaryotic cells with exogenous nucleic acid sequences is common knowledge to a specialist in the field of molecular biology.

In another embodiment of this invention the cell in accordance with the invention can, however, also be a eucaryotic cell like a fungus cell (for example yeast) or an animal cell. Methods for transformation or transfection of eucaryotic cells with nucleic acid sequences are likewise common knowledge to the specialist in the field of molecular biology.

The invention also concerns cell cultures that have at least one of the host cells in accordance with the invention, where the cell culture in accordance with the invention is in particular capable of producing an SDH and optionally a sucrose mutase.

The invention also concerns a method for producing an SDH, where the host cell in accordance with the invention is cultured in a culture medium under conditions that allow the formation of the SDH and under which the SDH can be recovered.

Another embodiment in accordance with the invention consists of proteins that are encoded by nucleic acid molecules in accordance with the invention, as well as methods for producing them, where the host cells in accordance with the invention are cultured under conditions that allow the synthesis of the protein and then the protein is isolated from the cultured cells and/or the culture medium.

In addition, the invention concerns monoclonal and polyclonal antibodies that are capable of identifying and optionally binding a structure of a unit in accordance with the invention having SDH activity. This structure can be a protein, carbohydrate as well as a lipid complex and/or glycolipid, which has a specific relationship to the unit that contains SDH. Also, antibodies that are directed toward structures that are matched to the SDH as posttranslational modifications are encompassed by the invention. It is important that a spatial electron cloud structure can be identified by means of antibodies so that it is possible to draw conclusions regarding the biological, chemical and physical properties of the unit having SDH activity.

In another particular embodiment the invention also concerns antibodies that react with the said antibodies in accordance with the invention, especially ones that can identify and bind these antibodies.

In addition, the invention concerns the said antibodies, where they are modified by biological, chemical and physical means.

The invention is to be illustrated below by means of examples and the pertinent figures.

EXAMPLES

SEQ ID No. 1 shows the amino acid sequence of SDH consisting of 262 amino acids, SEQ ID No. 2 shows the nucleotide sequence of SDH consisting of 789 nucleotides, SEQ ID Nos. 3 to 9 show partial amino acid sequences of SDH.

EXAMPLE 1

Preparation of SDH

Biomass Production of *Gluconobacter suboxidans*

To make available sufficient biomass of *Gluconobacter suboxidans* DSM 2003, the string was fermented on a laboratory scale. The following was used as a medium 1: D-mannitol (50 g/L), peptone from casein (10 g/L), yeast extract (5 g/L) and $CaCO_3$ (20 g/L). A medium 2 was composed as follows: D-mannitol (75 g/L), peptone from casein (16 g/L), yeast extract (8 g/L) and $CaCO_3$ (1 g/L).

A freeze-dried preparation of strain *Gluconobacter suboxidans* DSM 2003 was suspended as preculture in 1 mL medium 1, smeared on an agar plate with medium 1 and cultured for 72 h at 25° C. Then a subculture of the agar plate culture was introduced into 25 mL medium 1 and cultured in a shaker flask for 48 h at 25° C. The culture, also called the first preculture, was then cultured in 250 mL medium 1 in a shaker flask (volume 1 L) for 48 h at 25° C. The culture obtained in this way, also called the second preculture, then served as inoculum for the fermentation.

For fermentation the second preculture was transferred from the shaker flask into 15 L of medium 2 in a 20 L fermenter and cultured at 25° C. under the following conditions:

pH value: 6.9 (kept constant by titration by 5 N NaOH)
Stirrer speed: 350 rpm, and
Oxygen saturation: 40%.

The said conditions were kept constant during the fermentation. The fermentation was terminated with the end of cell growth, which was established from the consumption of the substrate by HPLC.

The resulting cell mass was harvested by centrifuging (8000 g, 20 min, 4° C.) and washed with a 0.9% NaCl solution and diluted in 50 mM tris-buffer (pH 7.0) 1:3 and then disintegrated in a French press process. The resulting cell fragments were removed by ultracentrifuging (110,000 g,20 min,4° C.). The clear supernatant, the so-called raw extract, was immediately used or was stored at −30° C.

Purification of the SDH

The following three-step scheme was chosen for purification of the SDH:

Step 1

The raw extract was applied to a DEAE sepharose column (2.6×9 cm) equilibrated with 50 mM tris/HCl buffer (pH 7.0) and eluted with a linear gradient of 0.0–0.5 M NaCl in 50 mM tris/HCl buffer (pH 7.0) at a flow rate of 50 cm/h. The SDH could be eluted at 0.2 M NaCl.

Step 2

A dye ligand affinity chromatography column was prepared as follows: (i) a Sepharose 4B-CL gel was used as matrix (Boyer, P. M. and Hsu, J. T. (1993) In: Fiechter, A. (ed.) Advances in Biochemical Engineering, 49, 1–44) and (ii) the dye Blue 160 (Blue H-ERD) was immobilized by the method of Neuhauser, W. et al., 1997 (Biochem. J., 326, 683–692). 10 mg dye per mL gel were used. The pooled SDH-containing fractions from step 1 were dialyzed and applied to the dye ligand column (2.6×7.0 cm, equilibrated with 50 mM tris/HCl buffer, pH 7.0) (about 2–5 mg protein/mL gel). The adsorbed protein was eluted with a linear gradient of 0.0–0.5 M NaCl in 50 mM tris/HCl buffer, pH 7.0 at flow rate of 2.0 mL/min. The SDH could be eluted at 0.1 M NaCl.

Step 3

The pooled active fractions from step 2 were dialyzed and concentrated by ultrafiltration and again applied to a dye ligand column (2.6×7.0 cm, equilibrated with 50 mM tris/HCl buffer, pH 7.0), applying about 0.5 mg protein per mL gel. The affinity elution of the pure SDH was carried out with 10 mM NADH in 20 mM tris/HCl buffer, pH 7.0, at a flow rate of 10 cm/h. The NADH was then removed by dialysis.

The purified SDH can be stored for about 8 months at −30° C. and the SDH is stable for about 30 days at +4° C.

TABLE 1

Purification scheme for the SDH

| Reinigungs-schritt | Gesamt-Aktivitat (U) | Gesamt-Protein (mg) | spezifische Aktivitat $(U \cdot mg^{-1})$ | Anreicherung (fach) | Aus-beute (%) |
|---|---|---|---|---|---|
| Rohextrakt | 360.0 | 782.6 | 0.46 | 1.0 | 100 |
| DEAE-Sepharose | 281.0 | 78.5 | 3.58 | 7.8 | 78 |
| Blue 160-Affigel | 174.0 | 15.7 | 11.12 | 24.2 | 48 |
| Blue 160-Affigel | 120.0 | 4.9 | 24.49 | 53.2 | 33 |

Key:
1  Purification step
2  Total activity
3  Total protein
4  Specific activity
5  Enrichment
6  Yield
7  (Factor of)
8  Raw extract By means of this purification scheme, thus separation of the raw extract by means of anion exchange chromatography, then a first dye ligand affinity chromatograhy, ultrafiltration, and second dye ligand affinity chromatography, enrichment by a factor of approximately 50 compared to the raw extract can be achieved. The yield is then about 33%.

Example 2:

Preparation of 1,6-GPS from Isomaltulose

Enzymatic Continuous Preparation of 1,6-GPS in an Enzyme Membrane Reactor

Continuous preparation of 1,6-GPS from isomaltulose was carried out using a stainless steel reactor (volume 50 mL). The enzyme membrane reactor had a double jacket for temperature control by means of water cooling, drillings for inserting a conductivity and pH electrode and connections for measuring pressure, supplying substrate, withdrawing product and taking samples. The magnetic stirrer situated inside the reactor, which can be operated externally, guarantees optimum mixing of the supplied substances. The top of the reactor had a metal sinter plate on the underside, on which an ultrafiltration membrane and an O-ring were mounted. After filling the reactor the top with its bottom part was screwed on. The substrate was supplied by means of a piston pump. The conductivity and pH value of the reaction solution were continuously and directly measured, with a control system keeping the pH value titrimetrically constant. Since ultrafiltration membranes do not guarantee complete retention of the coenzyme, a charged membrane made by the Nitto Co. (Nitto Membrane NTR-7410) was used. This electrostatic method of coenzyme retention also guarantees that dissociated coenzymes will remain in the desired reaction space.

The described membrane reactor was filled with a solution of 250 mM isomaltulose and glucose in 50 mM tris/HCl buffer, pH 7.5 (+0.1% $NaN_3$). The reactor was then operated at a flow of 2 mL/h for 24 h at "idle" in order to detect and, if necessary, remedy any leaks or other problems. Then SDH and the regeneration enzyme FDH were introduced with a superloop, as is used for sample input in chromatography. At the beginning of the reaction 1 U/mL each fully purified SDH (from Example 1) and GDH (glucose dehydrogenase from Bacillus megaterium) were used. The reaction was initiated by injection of 2.5 □m $NAD^+$. The pH was kept constant at 7.0 by titration with 1 M tris. An important factor in the operation of a continuous reactor is the residence time distribution. This is calculated, assuming optimum mixing of the reaction solution, by the formula $t=[V]/V_0$, where V is the reactor volume and $V_0$ is the volumetric flow rate. After four hours of a batch experiment the substrate feed was adjusted to a flow of 2 mL/h so that the average residence time (t) was 25 h. The test duration as 234 h, and the enzyme activities, alkali consumption, conductivity, pressure, substrate and product volume were determined at regular intervals. The product samples that were taken were tested by HPLC for their composition and the formation of 1,6-GPS.

EXAMPLE 3

Enzymatic Single Bioreactor Process ("One-Pot Reaction") for Production of 1,6-GPS from Sucrose A batch experiment with immobilized cells of P. rubrum and the enzyme SDH from G. suboxidans 2003 and FDH from Candida boidinii was carried out under the conditions listed below for direct enzymatic preparation of 1,6-GPS from sucrose. The substrates in this reaction were sucrose and ammonium formate.

| | |
|---|---|
| Volume: | 10 mL |
| Temperature: | 25° C. |
| Sucrose: | 500 mM |
| Formate: | 500 mM |
| P. rubrum cells: | 1 g |
| SDH | 5 U |
| FDH: | 10 U |
| NAD: | 1 mM |

Since the pH value increased during this reaction, it was constantly adjusted to a pH of 7.0 with 1 M formic acid. The substrate consumption was monitored during the reaction by DC and DNS methods (for the conversion of sucrose to isomaltulose) and HPLC (for the conversion of isomaltulose to 1,6-GPS). It is possible to demonstrate the direct formation of 1,6-GPS from sucrose in one reaction vessel and one process step.

Example 4

Nucleic Acid and its Derived Peptide Sequence of SDH

1. Peptide Sequence Determination

To determine partial amino acid sequences, the SDH of Gluconobacter suboxidans DSM 2003 purified in accordance with Example 1 was tryptically digested and separated by standard methods. The resulting partial peptide sequences are represented in SEQ ID Nos. 3 through 9.

2. DNA Probe Preparation

Primers were prepared on the basis of the sequences analyzed in the peptide sequence determination and used for cloning of the complete gene of the SDH from Gluconobacter suboxidans DMS 2003.

3. Creation of the Gene Bank and Clone Isolation

The said primers (SEQ ID Nos. 3 and 5) were used in a PCR reaction and a fragment of the SDH-coding sequence was obtained. A DNA probe was prepared with the PCR fragment. After labeling the probe, hybridizing bands were established in a genomic southern blot. Two independent subgenomic gene banks (~9 kb fragment after ClaI digestion, ~3.5 k6 fragment after BamHI digestion, purification of fragments by sucrose gradient centrifugation) with purified fragment shares were established in pBlueskrip SK. The subgenomic clone banks were tested by hybridization with the said labeled probe. Several clones were identified of which one clone of each of the BamHI and ClaI banks was further analyzed.

4. Sequence Analysis

Sequence determination of the clone fragments in both cases gave a corresponding DNA sequence. From this it was possible to establish the amino acid sequence of the SDH. It corresponds with the sequences from the peptide sequences, up to the position Codon 196, for which the peptide sequence for peptide 5 now has serine (S) instead of the now determined tryptophan (W 196).

The nucleotide sequence of the SDH of Gluconobacter suboxidans DSM 2003 is represented under SEQ ID No. 2 and includes 789 nucleotides.

The amino acid sequence of the sorbitol dehydrogenase of Gluconobacter suboxidans DSM 2003 is represented under SEQ. ID No. 1 and includes 262 amino acids.

5. Expressions in *E. Coli*

Figure 1:
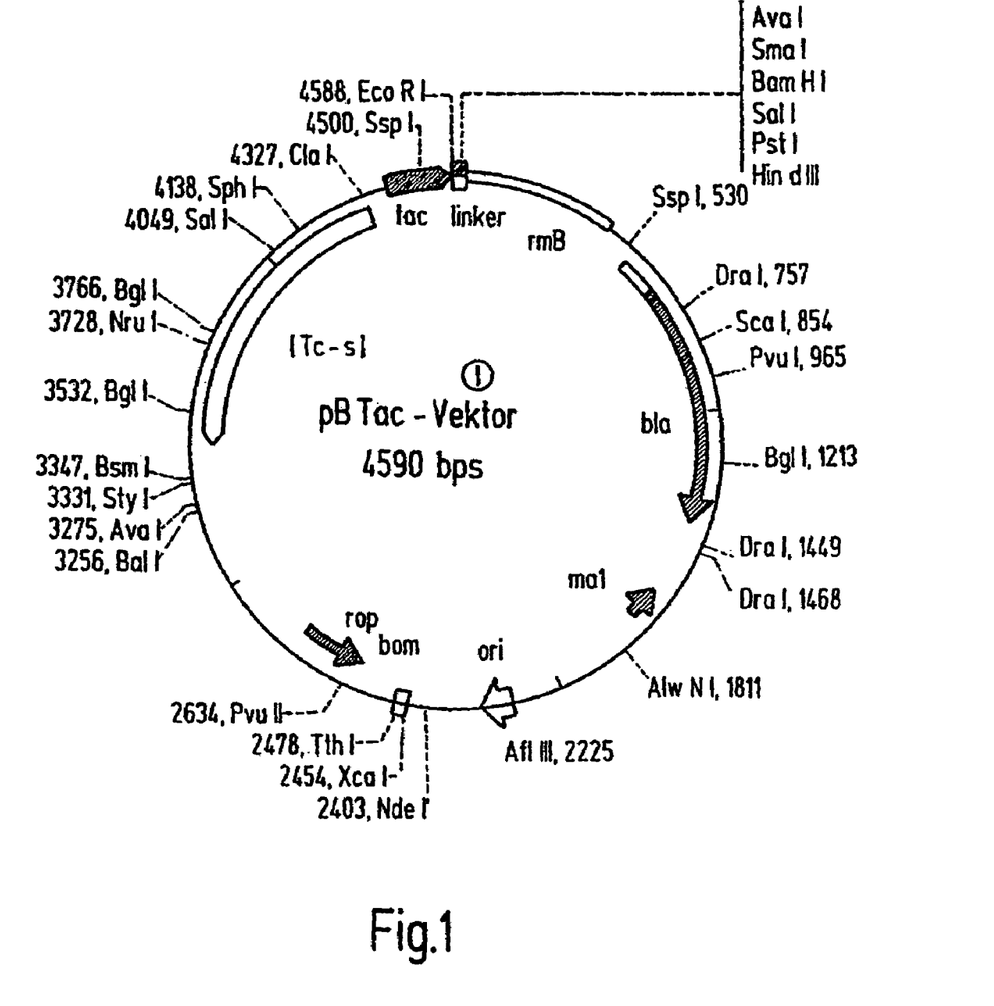
FIG. 1: a plasmid map of the plasmid pBtac 2.
Figure 2:
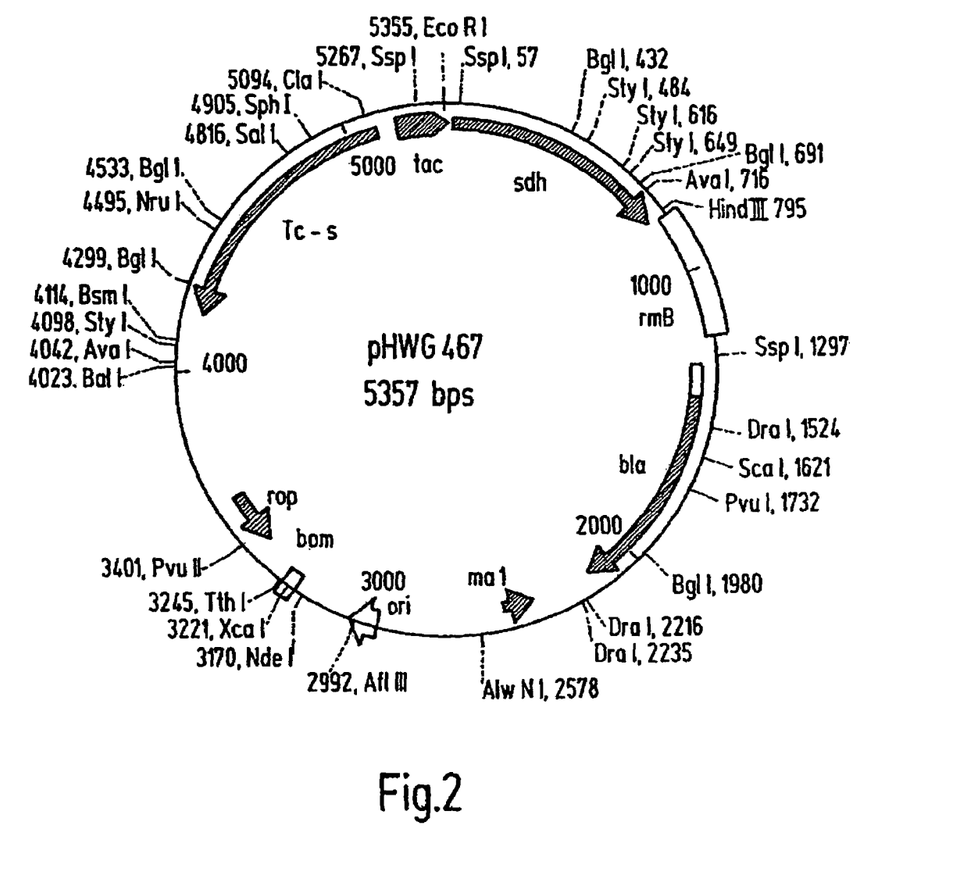
FIG. 2 shows a plasmid map of pHWG 467.

The coding sequence was lengthened at the 5' end with the sequence GAATTCTT and at 3' end with the sequence AAGCTT. This sequence was integrated into the vector pBtac2 (FIG. 1; J. Bosius (1988), Biotechnology 10, 205–225), which had been prepared with EcoRI and HindIII. The resulting plasmid pHWG 467 (FIG. 2) contains an ampicillin resistance gene and the SDH-coding sequence under control of the tac-promoter. Plasmid pHWG 467 was transformed in *E. coli* JM109. These cells produce SDH activity after induction with IPTG. The activity of the corresponding protein can be determined in the raw extracts. In the SDS gel of these extracts the protein is stainable as a dominant and at 28 kDa with Coomassie Brilliant Blue.

---

The invention claimed is:

1. A method for enzymatic preparation of 6-O-α-D-glucopyranosyl-D-sorbitol (1,6-GPS) from isomaltulose, comprising providing an aqueous reaction solution of isomaltulose containing a unit having sorbitol dehydrogenase (SDH) activity, incubating the solution, and then recovering 1,6-GPS from the reaction solution.

2. A method as in claim 1, wherein reduction equivalents are added to the aqueous reaction solution before or during the incubation.

3. A method as in claim 1, wherein the unit having SDH activity is isolated SDH.

4. A method as in claim 1, wherein the unit having SDH activity is a living or dead microorganism containing SDH or a raw extract thereof.

5. A method as in claim 4, wherein the microorganism containing SDH is *Gluconobacter suboxidans* DSM 2003.

6. A method as in wherein the method is carried out with or without pH value regulation.

7. A method as in claim 5, wherein a regeneration agent is added to the aqueous reaction solution before or during the incubation.

8. A Method as in claim 7, wherein the microorganism, the raw extract or the enzyme is immobilized.

9. A method as in claim 8, wherein the method is carried out continuously.

10. A method as in claim 9, wherein the isomaltulose used as starting material is prepared by enzymatic conversion of sucrose to isomaltulose.

11. A method as in claim 10, wherein the enzymatic conversion of sucrose to isomaltulose is carried out by means of immobilized *P. rubrum* cells, isolated sucrose mutase, a cell digest of *P. rubrum* or a mixture thereof.

12. A method as in claim 11, wherein the enzymatic conversion of sucrose to isomaltulose and of isomaltulose to 1,6-GPS takes place in a single process step.

13. A method as in claim 12, wherein the conversion of sucrose to isomaltulose and of isomaltulose to 1,6-GPS is carried out in a single bioreactor.

14. A method as in claim 13, wherein the enzymatic preparation takes place at temperatures from 20°C. to 40°C.

15. A method for enzymatic preparation of 1,6-OPS from sucrose, wherein sucrose is enzymatically converted to isomaltulose and subsequently or simultaneously the isomaltulose is enzymatically converted to 1,6-GPS by means of a method as in claim 1 to 6.

* * * * *